(12) United States Patent
Johns

(10) Patent No.: US 12,033,747 B2
(45) Date of Patent: *Jul. 9, 2024

(54) METHODS, DEVICES AND SYSTEMS FOR MEDICAL CODE EVENT INFORMATION TRACKING

(71) Applicant: Brooke Johns, Henderson, NV (US)

(72) Inventor: Brooke Johns, Henderson, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/216,300

(22) Filed: Jun. 29, 2023

(65) Prior Publication Data
US 2024/0047050 A1 Feb. 8, 2024

Related U.S. Application Data

(63) Continuation of application No. 17/161,477, filed on Jan. 28, 2021, now Pat. No. 11,694,793.

(60) Provisional application No. 63/111,684, filed on Nov. 10, 2020, provisional application No. 62/967,138, filed on Jan. 29, 2020.

(51) Int. Cl.
*G16H 40/20* (2018.01)
*A61B 5/00* (2006.01)
*G16H 20/00* (2018.01)

(52) U.S. Cl.
CPC ............ *G16H 40/20* (2018.01); *A61B 5/742* (2013.01); *A61B 5/747* (2013.01); *G16H 20/00* (2018.01)

(58) Field of Classification Search
CPC ........ G16H 40/20; G16H 20/00; G16H 15/00; G16H 10/60; A61B 5/742; A61B 5/747; A61B 5/02
See application file for complete search history.

(56) References Cited

U.S. PATENT DOCUMENTS

| 6,314,384 | B1 | 11/2001 | Goetz | |
|---|---|---|---|---|
| 11,694,793 | B2 | 7/2023 | Johns | |
| 2008/0162188 | A1* | 7/2008 | Kripalani | G16H 20/10 705/3 |
| 2009/0254365 | A1 | 10/2009 | Gravina | |
| 2013/0024213 | A1* | 1/2013 | Poon | A61B 5/411 705/3 |

(Continued)

OTHER PUBLICATIONS

Medicine, "Impact of a New Medical Record System for Emergency Departments Designed to Accelerate Clinical Documentation," vol. 94, No. 26, Jul. 2015, www.md-journal,com, 6 pages.

(Continued)

*Primary Examiner* — Quan Zhen Wang
*Assistant Examiner* — Rajsheed O Black-Childress
(74) *Attorney, Agent, or Firm* — WEIDE & MILLER, LTD.

(57) ABSTRACT

A device is configured to process medical-event related information, such as associated with a medical code event, such as by receiving medical-event related information, recording medical event information with timestamps, generating additional medical information, displaying medical events and additional medical information on media display, visual indicators, and user devices to provide real-time notifications of recorded and reminders for upcoming medical events, and sending medical events with timestamps and additional medical information to other devices for further processing. The device may be configured as a code clock which includes an analog clock.

20 Claims, 7 Drawing Sheets

(56) References Cited

U.S. PATENT DOCUMENTS

| | | |
|---|---|---|
| 2013/0085771 A1 | 4/2013 | Ghanbari |
| 2013/0325508 A1 | 12/2013 | Johnson |
| 2014/0310014 A1 | 10/2014 | Banerjee |
| 2015/0007294 A1 | 1/2015 | Wang |
| 2015/0302150 A1 | 10/2015 | Mazar et al. |
| 2015/0379199 A1 | 12/2015 | Tambasco, Jr. |
| 2016/0204937 A1 | 7/2016 | Edwards |
| 2017/0004261 A1 | 1/2017 | Abou-Hawi |
| 2019/0088353 A1 | 3/2019 | Humphrys |
| 2020/0121199 A1* | 4/2020 | Freeman .................. G06F 3/14 |
| 2020/0411184 A1* | 12/2020 | Swart .................... G06N 20/00 |
| 2021/0154102 A1* | 5/2021 | Berlin .................. A61J 7/0454 |

OTHER PUBLICATIONS

Gordon et al., "Accuracy Evaluation of Emergency Department Tracking System Timestamps," Ann Emerg Med. Nov. 2008 ; 52(5): 504-511. doi:10.1016/j.annemergmed.2007.11.036, 15 pages.

PR Web, "MEDI+SIGN Announces Digital Whiteboard Solution for Emergency Departments," https://www.medicaldesignandoutsourcing.com/medisign-announces-digital-whiteboard-solution-for-emergency-departments/, Dec. 30, 2016, 12 pages.

Ornato et al., "The electronic clipboard: an automated system for accurately recording events during a cardiac arrest," https://pubmed.ncbi.nlm.nih.gov/7469153/, 1 page.

\* cited by examiner

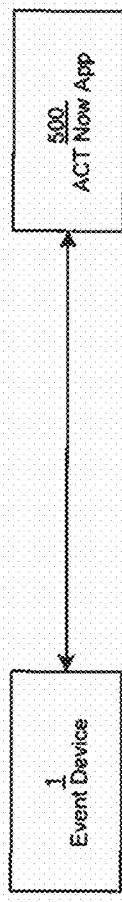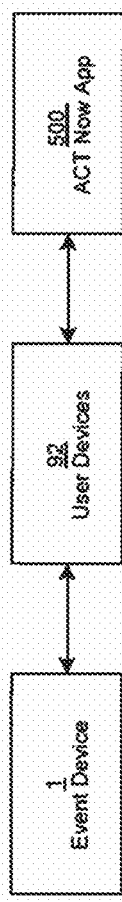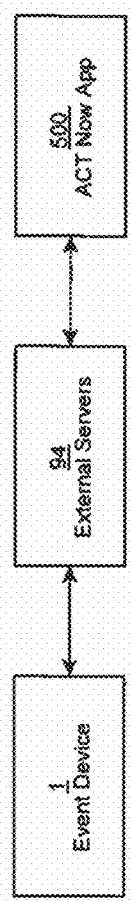

METHODS, DEVICES AND SYSTEMS FOR MEDICAL CODE EVENT INFORMATION TRACKING

RELATED APPLICATION DATA

The present application is a continuation of U.S. application Ser. No. 17/161,477, filed Jan. 28, 2021, which claims priority to U.S. Provisional Application Ser. No. 63/111,684, filed Nov. 10, 2020, and U.S. Provisional Application Ser. No. 62/967,138, filed Jan. 29, 2020, which prior applications are incorporated herein by reference in their entirety.

FIELD OF THE INVENTION

The present invention relates to medical devices.

BACKGROUND OF THE INVENTION

Hospitals frequently use code names to alert staff to various events, and particularly emergency events. The hospital may communicate a particular code, such as through an intercom system, in order to direct appropriate staff to respond to the event ("code event"). For example, a "Code Blue" event typically designates a medical emergency, such as cardiac or respiratory arrest.

In such an emergency event, a medical team may respond to a patient, such as in their hospital room, an ER or the like. The team might be comprised of one or more doctors, one or more nurses, a pharmacist, etc.

As with any medical procedure, it is desirable to record information about the patient and the actions taken by the medical personnel. Generally, such information is logged manually, such as by writing actions or information on a paper ledger. However, an emergency event is generally very time-sensitive, wherein the medical team is attempting to perform a variety of life-saving actions in a very short period of time. Further, a variety of members of the team may be performing different actions at different times. As a result, in these and other situations, various information may not be accurately captured, including by failing to log certain actions entirely, by logging incorrect information about the time an event occurred or action was taken, personnel involved, etc.

A solution to these and other problems is desired.

SUMMARY OF THE INVENTION

The described invention is an innovative solution to the problem of errors and omissions resulting logging medical events manually during code events.

Embodiments of the invention comprise methods, systems, and devices of processing medical-event related information, such as receiving medical-event related information, recording medical event information with timestamps, generating additional medical information, displaying medical events and additional medical information on media display, visual indicators, and user devices to provide real-time notifications of recorded and reminders for upcoming medical events, and sending medical events with timestamps and additional medical information to other devices for further processing. One embodiment of the invention is a device in the form of an analog clock.

As an aspect of the invention, a plurality of systems and devices may be in direct or indirect communication with each other to send and receive medical-event related information, timestamps, and additional medical information generated by any one of such systems or devices, such that the media displays and visual indicators on each of the plurality of devices may display information sent by any one of the plurality of systems or devices.

As another aspect of the invention, medical-event related information may be sorted into confidential medical information and non-confidential medical information, and confidential medical information is recorded and sent with additional security protocols and features to protect patient confidentiality.

Likewise, in accordance with such a system, the plurality of devices in communication with each other to send and receive medical-event related information may be sorted into devices of various clearance levels, such that devices of certain clearance levels may send, receive, and display all confidential medical information, while devices of different clearance levels may send, receive, and display some or no confidential medical information.

Further objects, features, and advantages of the present invention over the prior art will become apparent from the detailed description of the drawings which follow, when considered with the attached figures and tables in the Appendix.

DESCRIPTION OF THE DRAWINGS

FIGS. 5A-C illustrate the event device in direct and indirect communication with the software application associated with the event device;

DETAILED DESCRIPTION OF THE INVENTION

The following description sets forth numerous specific details to provide a more thorough description of the present invention. It will be apparent, however, to one skilled in the art, that the present invention may be practiced without these specific details. In other instances, well-known features have not been described in detail so as not to obscure the invention.

Aspects of the invention comprise methods, devices and systems for tracking or recording information associated with medical events, such as information associated with a patient medical event, and preferably a medical code event, relative to one or more associated personnel such as medical personnel (doctors, nurses, surgeons, etc.).

Figure 1:
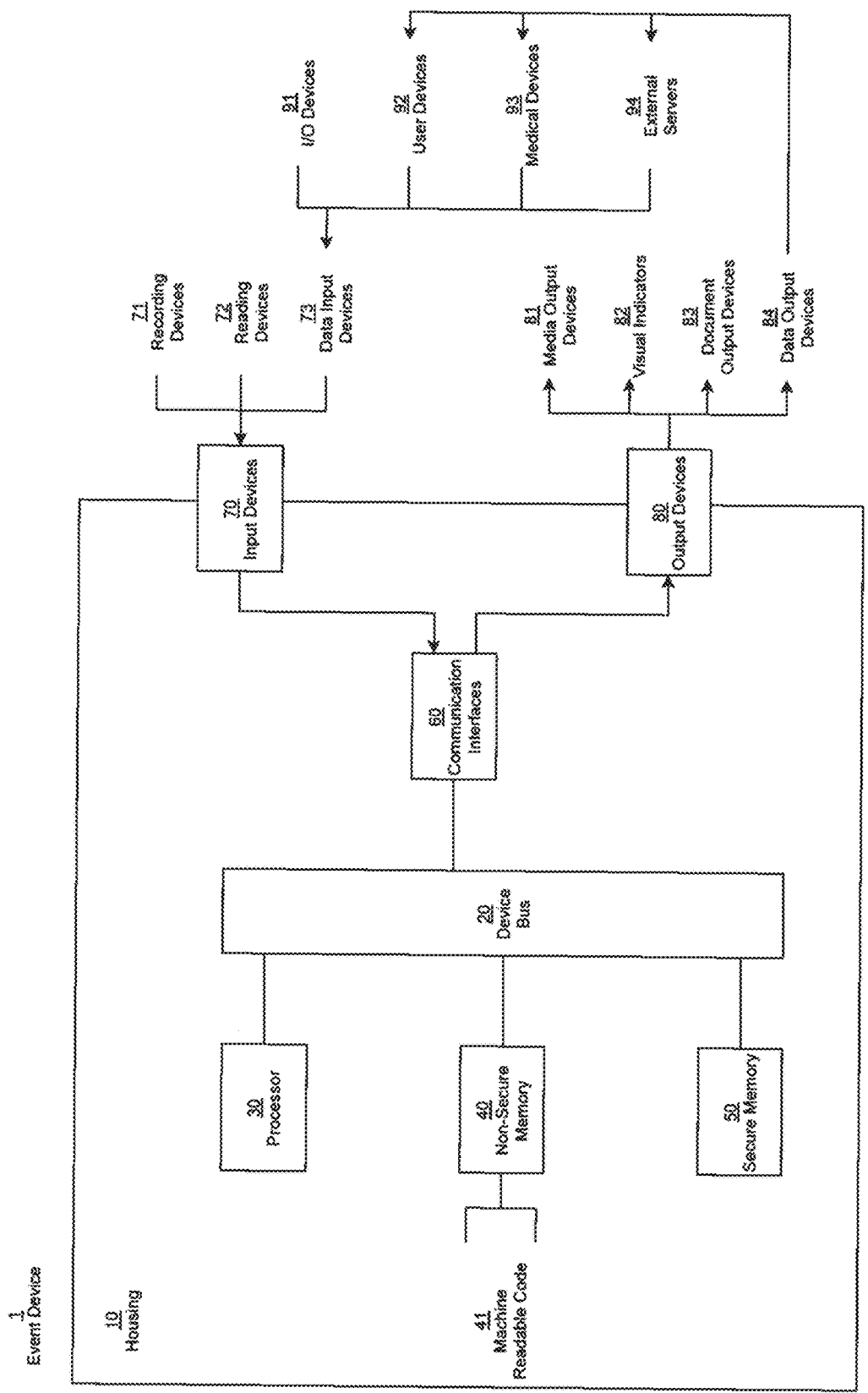
FIG. 1 schematically illustrates internal components of an event device.

FIG. 1 illustrates one embodiment of an event device 1 in accordance with an embodiment of the invention. In one embodiment, the event device 1 comprises various electronic components in communication with one another through a device bus 20. The electronical components may comprise a processor 30, a non-secure memory 40, a secure memory 50, one or more communication interfaces 60 used to communicate with one or more input devices 70 and one or more output devices 80. One or more of the components of the event device 1 may be associated with a housing 10, such as by being contained within or mounted to the housing 10.

The non-secure memory 40 stores machine-readable code 41. The secure memory 50 stores medical event information. In one embodiment, the secure memory 50 may include read and/or write protect features to control access to the stored information. One embodiment of such read and/or write protect feature is requiring a user to enter a password or other authorization to access, modify or delete information associated with the secure memory 50.

The CPU or processor 30 executes the machine-readable code 41. In one embodiment, the CPU or processor may be configured to encrypt information routed to the secure memory 50.

Input devices 70 may comprise recording devices 71 (such as microphone, cameras, sensors, etc.), reading devices 72 (such as magnetic stripe reader, chip reader, RFID tag reader, or optical scanner, etc.), and one or more data input devices 73. Data input devices 73 may comprise one or more input/output (I/O) devices 91, one or more user devices 92, one or more medical devices 93, and/or one or more external servers 94.

I/O devices may comprise keyboard, mouse, button pad, touch screen, I/O ports, etc. Such I/O interfaces may be of various types, such as wired (USB, DVI, HDMI, multi-pin serial or parallel, etc.) and/or wireless (Bluetooth, Wi-Fi, etc.).

User devices 92 may comprise smartphones, tablets, computers, etc., or interface for interfacing to such user devices 92.

Medical devices 93 may comprise devices used to measure patient data or values (such as heart monitor, blood pressure monitor, electrocardiogram, etc.) and/or devices used to apply medication or treatment.

External servers 94 may implement databases to process and/or store information and provide interface to communicate with such databases, such as websites. For example, the record of information associated with a code event of a patient might be transmitted from the event device 1 to a patient's electronic hospital record for association therewith.

Output devices 80 might comprise media output devices 81 such as one or more visual or video displays (such as CRT, plasma, LCD, LED, OLED, etc.) and/or one or more audio output devices (such as one or more speakers), one or more visual indicators 82 (such as one or more indicator lights, which lights might be of one or more colors, including different colors, and/or capable of being illuminated at differing brightness), one or more document output devices (such as printers, fax machines, etc.), and/or one or more data output devices 84 (such as one or more user devices 92, one or more medical devices 93, and/or one or more external servers 94).

Communication between one or more communication interfaces 60 with one or more input devices 70 and/or one or more output devices 80 may be wired (via a cable or ethernet) or wireless (via a network such as the Internet, a hospital LAN or WAN, etc.), and uses various communication protocols, including TCP/IP or others.

In some embodiments, components of the event device 1 might not be associated with the housing 10. For example, if the event device 1 includes an I/O device 91 such as keyboard and mouse, such devices might be located on a work surface near the event device 1, such that the mouse and keyboard communicate with the event device 1 via the communication interfaces 60.

Although not illustrated, the event device 1 may be powered by a primary power supply, such via an electrical outlet, and include a secondary or back-up power supply, such as one or more batteries.

In one embodiment, the operation of the event device 1 can be initiated through information via input devices 70, such as information associated or related to a code event. In one embodiment, code events communicated to input devices 70, such as by voice command through a recording device 71 or touch command through an i/o device 91 or user device 92, might automatically trigger the event device 1 to start recording information.

Upon proper initiation, the event device 1 is preferably configured to receive information regarding persons (including the patient and/or associated medical personnel) associated with a medical event, such as a medical code event, via input devices 70.

In one embodiment, the event device 1 is configured to receive information regarding staff personnel present at the code event. Such information might include RFID tags of medical personnel who are in the vicinity of the event device 1, magnetic stripes on personnel badges, etc.

In one embodiment, the event device 1 is configured to receive patient information. Such information might include patient IDs (such as a barcode or label) of patients in the vicinity of the event device 1. In one embodiment, patient information received by the event device 1 may prompt the event device 1 to communicate with external servers 94 to retrieve additional information regarding patient data or values (such as patient height, weight, medical history, etc.).

In one embodiment, the event device 1 is configured to receive information via input devices 70 regarding activities occurring during a code event. The form of such information might include voice input (such as voice commands), audio input (such as recorded audio), visual input (such as recorded pictures and/or videos), touch input, or input from external medical devices (such as heart monitor, blood pressure monitor, electrocardiogram, etc.). The content of such information might include occurrence of medical events (such as application of treatment and medication), media recordings of medical events (such as audio, image, or video recordings), patient data or values (such as heart rate, blood pressure, etc.), and or media recordings of patient data or values (such as audio, image, or video recordings of patient appearance or behavior).

The event device 1 preferably stores the information received in the secure memory 50. Where applicable, the event device 1 preferably applies timestamps to the stored information, such as to document the occurrence of certain events or activities and their respective time of occurrence.

In one embodiment, the event device 1 may use patient data or values to customize the desired medication or treatment or otherwise generate and output additional medical information based upon the received medical event information. For example, during a code event comprising pediatric arrest, the event device 1 may retrieve the patient data or values from external servers 94, as discussed above, then use some of the retrieved information, such as the patient's weight in Kg, to calculate the correct dosage of a desired medication based upon the patient's weight. As discussed above, the event device 1 may also receive such patient data or values through other input devices 70.

In one embodiment, the event device 1 communicates with data output devices 85 to report recorded information and/or to request additional information.

In an embodiment, the event device 1 may cause document output devices to print information event strips after recording of a code event has terminated.

In one embodiment, the event device 1 may be configured to display information through output devices 70. Displayed information include patient data or values (such as heart rate, heart rhythm), a list of medication administered and their respective time of administration, calculated timing of upcoming medications to be administered and/or recommended medications from external devices.

As one example, during a particular code event, the event device 1 might receive a list of administered medication through its input devices 70, record the list of medication with timestamps, and display said list of administered medication through its output devices 80. Simultaneously, the event device 1 might automatically calculate the timing for the next application of some or all the medications on the list of medications the event device 1 recorded. Upon calculating the timing, the event device 1 might then display alerts when the medication is to be administered via the output devices 80 (such as display of visual or audio notification 81, visual indicators 82, alerts to user devices 92, or notifications to medical devices 93, etc.).

As another example, during a particular code event, the event device 1 might communicate with a first external server 94 to deliver information regarding patient data or values indicating the necessity for immediate treatment. The event device 1 might then receive information from said first external server 94 identifying the best medications or other treatments and associated dosing and the scheduling of such medications or treatment. The event device 1 might, upon receiving such identification, communicate with a second external server 94 to provide instruction for such medication or treatment, and simultaneously display alerts when recommended medication is to be administered via other output devices 80.

As another example, during a particular code event, the event device 1 might receive information from an external server 94 which identifies medications or other treatments to be administered. The event device 1 might identify an interaction problem such as overlapping or conflicting medications or treatments. The event device 1 might then communicate such problem to the external server 94. In this manner, the event device 1 may serve as a "smart" device relative to the activities which are occurring during the particular code event.

In one embodiment, the event device allows the user to recall recorded information. For example, if the user wishes to determine whether the medication epinephrine was given, and if so, when, or how many times, the user may activate the recall feature through the one or more input devices 70. Upon proper input to select the information the user wishes to recall (in this case, the application of epinephrine to the patient), the event device 1 may cause the output devices 80 to provide audio feedback and/or visual display of the information (for example, an audio read-out and/or a video or image display of whether epinephrine was given, and if so, when and how many times).

In another embodiment, the machine-readable code/software 41 in the event device 1 (alone or as coupled to external systems or servers) may be updated with new algorithm and/or information regarding current best practice in treatments and medication.

Figure 2:
FIG. 2 illustrates the external components of one embodiment of the event device.

FIG. 2 illustrates one embodiment of the event device 1. In this embodiment, the event device 1 is configured as an event clock 100, which has a form similar to a clock. In the preferred configuration, the event clock 100 is an analog clock with moving physical hands 110 and traditional indicators and numbering to display time 111. In other embodiments, the event clock 100 might be displayed as a graphical representation on a display or a portion of a display.

The event clock 100 might thus be mounted on a wall, such as within a hospital patient room, hospital emergency room, etc. The output devices 80 may be located at the front of the event clock 100, while the remaining components in housing 10 may be located at the back of the event clock 100.

In one embodiment, the event clock 100 is configured to display one or more icons regarding particular events or event-related information, such as an icon that indicate compressions 120 (such as via a "CPR" icon or symbol), shocks 130 (such as via a "lightning bolt" icon or symbol), pulse checks 140 (such as via a "heart" icon or symbol), and heart rhythms observed 150 (such as via a EKG icon or symbol).

In one embodiment, icons such as CPR 120, shocks 130, and pulse checks 140 will glow while the specific treatment or measurement is being performed. In another embodiment, icons such as CPR 120, shocks 130, and pulse checks 140 will change color, along with audio prompts via output devices 80, to provide secondary information. For example, after receiving information from input devices 70 indicating a compression should be performed, the CPR icon 120 might blink for 2 minutes to indicate the appropriate duration of compression. As another example, 2 minutes after the application of compression, the pulse check icon 140 might blink to notify a pulse check following compression is due.

In one embodiment, a number indicator 131 below the shocks icon 130 indicates the number shocks applied to the patient.

In one embodiment, intervening events and inputs may cause a base configuration of the event clock 1 (or its output) to be modified. For example, relative to the above example, the base configuration might be for the CPR icon 120 to blink for 2 minutes upon receiving information from input devices 70 indicating a compression should be performed for 2 minutes. On the other hand, if the event device 1 receives information from input devices 70 that compression was performed for 3 minutes and then a STAT echo was performed to check heart activity, the event device 1 might cause the blinking light in the CPR icon 120 to turn off and not turn on again without further prompts.

In one embodiment, the media output devices 81 include a speaker on the front of the event clock 132 to allow better audio output, particularly for the recall feature discussed above.

In one embodiment, various output devices 70 on the event clock 100 provide visual and audio feedback for medications. One preferred embodiment is a set of visual indicators 82 comprising of light indicators 160. In one embodiment, the light indicators 160 comprise one or more lights positioned relative to the time indicators 111, such as at each 1-minute interval of the clock. In one embodiment, each light on the light indicators 160 is capable of displaying different colors to indicate different color-coded medications. In another embodiment, instead of circular dots, the light indicators may comprise letters to display the first letter of a particular medication.

The light indicators 160 may be activated in various manners to provide medication-related information. For example, a solid light may indicate that a particular medication is available to be given at the designated time. A blinking light may indicate that a particular medication is due at a particular time. Such blinking light may continue to blink, following the minute hand 110 as it sweeps, until the event device 1 receives information from its input devices 70 that medication is given or cancelled, or the event code is terminated.

In one embodiment, the event clock 100 may comprise audio output devices 81. In one preferred embodiment, the event clock 100 comprises an audio device 81 configured to emit at least two alert sounds. One alert sound may comprise a "due soon" alert to indicate that a medication is due within a designated amount of time (such as 30 seconds). The other alert sound may comprise a "due now" alert, indicating that a medication is due. Such alert sounds are preferably short chirps, lasting about three to five seconds.

In one embodiment, if the event device 1 does not receive information that medication is given when due, after the alert sound expires, the event clock 100 may continue to display a visual indicator 82 such as a light indicator 160.

In one embodiment, termination of operation of the event clock 1 may be initiated by input received from input devices 70.

In one embodiment, the event device 1 may communicate with one or more user devices 92. In the case where the user device 92 is one or more mobile communication device (such as a smartphone, a tablet, a smartwatch, etc.), the invention provides a uniquely configured ACT Now software application ("ACT Now App") 500 which the user can download and install on such mobile communication device.

Figure 3:
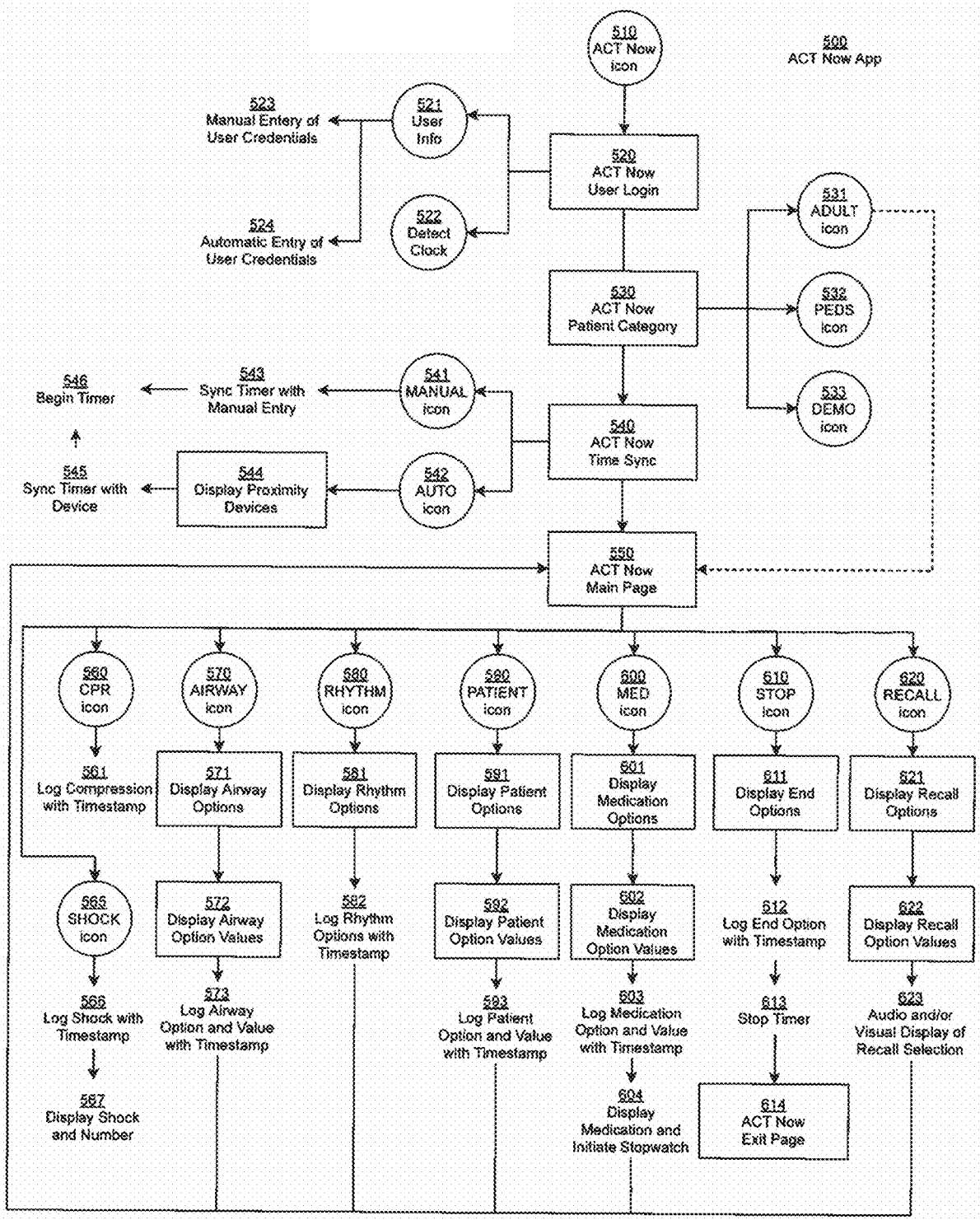
FIG. 3 illustrates the flow diagram of the software application associated with the event device.

FIG. 3 illustrates a flowchart of one embodiment of the ACT Now App 500 comprising of an ACT Now icon 510, a user login page 520, a patient category selection 530, and time sync feature 540, a main page 550, and an exit page 614.

In a preferred embodiment, each user input, selection, or command in the ACT Now App 500 can performed with voice commands.

The user login page 520 allows user to provide user credentials 521 via manual input 823 (such as username and password, identification code, etc.) or via readable information 524 (such as a badge, barcode, or QR code 524, which the ACT Now App 500 may scan or read).

The user login page also allows user to initiate communication 522 between the ACT Now App 500 and the communication interfaces 60 of any event devices 1 in proximity.

The patient category selection 530 allows users to select "ADULT" 531 for adult patients, "PEDS" 532 for underaged patients, and "DEMO" 533 for a teaching mode where various code events may be rehearsed for learning purposes and no critical information will be stored. Proper section of patient category 530 will prompt the ACT Now App 500 to load features corresponding to each selection.

The time sync 540 feature allows users to sync the ACT Now App 500 timer, which the ACT Now App 500 uses to apply timestamps to recorded events, where applicable. The user can sync the ACT Now App 500 timer either via manual entry 541 (where the user can manually enter the current time 543) or automatic entry 542 (where the ACT Now App 500 will display devices in its proximity 544, and upon proper selection of proximity devices, the ACT Now App 500 will automatically sync its timer with the time used by the selected proximity device). Upon proper sync of the ACT Now App 500 timer, the ACT Now App 500 will begin its timer 546.

In one embodiment, the main page 550 might be configured to display a wide variety of other information and/or implement other functionality. For example, the ACT Now App 500 might be configured to replicate the information the event device 1 receives via its input devices and/or to display information the event device 1 displays via the output devices 80.

In one preferred embodiment, it may be desirable that the event device 1 not display detailed patient data or values to protect a patient's private information. Thus, in one embodiment when one or more ACT Now Apps 500 are included, the event device 1 might only display general information, such as time, etc., and the event device 1 or the associated system may be configured to cause each ACT Now App 500 to display any detailed patient data or values (including information about the patient or associated events, drugs, or procedures, etc.). For example, a nurse might administer a drug to a patient. The nurse might provide a voice input to the event device 1 regarding the administered drug. The event device 1 may process that information, including time stamping and storing the event information. However, the event device 1 might not display information regarding the event. Instead, information regarding the administered drug might only be displayed on ACT Now App 500.

In one embodiment, the ACT Now App 500 may provide functional back-up to the event device 1. For example, if the event device 1 malfunctions and fails to receive information via its input devices 70, the user may manually enter that information to the ACT Now App 500. Similarly, if the event device 1 malfunctions and fails to display information via its output devices the ACT Now App 500 may continue to display information to the user.

As one example, upon applying compression to a patient, the user can touch the CPR icon 560, prompting the ACT Now App 500 to record the event with timestamp 561. In one embodiment, the ACT Now App 500 may deliver the recorded information to an event device 1 and other output devices 80.

As another example, upon applying treatment to patient airway (such as bag valve masks or ventilator), the user can touch the AIRWAY icon 570, prompting the ACT Now App 500 to display a list of airway options 571, allowing the user to select common airway treatment. Where applicable, the selection of an airway option might prompt the ACT Now App 500 to display a list of values related to the selected airway option 572, allowing the user to record the airway option values (for example, the length of endotracheal tube used for intubation). Upon proper input of airway option and airway option values, the ACT Now App 500 may record the input with timestamp 573. In one embodiment, the ACT Now App 500 may deliver the recorded information to an event device 1 and other output devices 80.

As another example, the user might want to periodically record patient data or values related to rhythm (such as pulse or electrocardiogram displays). The user can touch the RHYTHM icon 580, prompting the ACT Now App 500 to display a list of rhythm options 581, allowing the user to select common patient data or values related to rhythm. Upon proper input of rhythm values, the ACT Now App 500 records the input with timestamp 582. In one embodiment, the ACT Now App 500 may deliver the recorded information to an event device 1 and other output devices 80.

As another example, the user might want to periodically record other patient data or values (such as blood pressure or blood sugar). The user can touch the PATIENT icon 590, prompting the ACT Now App 500 to display a list of patient data or values 591, allowing the user to input common patient data or values not related to rhythm. Upon proper input of patient data or values not related to rhythm, the ACT Now App 500 records the input with timestamp 592. In one embodiment, the ACT Now App 500 may deliver the recorded information to an event device 1 and other output devices 80.

As another example, the user might want to record medications or treatment given to the patient. Upon touching the MED icon 600, the ACT Now App 500 might display a list medication options 601, allowing the user to select common medications or procedures. Where applicable, the selection of a medication option might prompt the ACT Now App 500 to display a list of values related to the selected medication 602, allowing the user to record the amount of medication applied. Upon proper input of medication option and medication value, the ACT Now App 500 records the input with timestamp 603. In one embodiment, the ACT Now App 500 may deliver the recorded information to an event device 1 and other output devices 80.

Where applicable, the ACT Now App 500 might also initiate a stopwatch and display the stopwatch, name of medication, and number of medication on its main page 550, and notify user of the next application of medication or treatment. For example, when the user properly inputs a first injection of epinephrine, the ACT Now App 500 might initiate a stopwatch, display "EPIx1" and the stopwatch on its main page 550. In an embodiment, the ACT Now App 500 might also display visual (such as blinking stopwatch timer and blinking "EPIx1" display) and/or audio (such as the "due soon" or "due now" alert sounds) prompts to notify the user of next injection of epinephrine at the appropriate time interval. Upon the second injection of epinephrine, the ACT Now App 500 might restart the stopwatch and display "EPIx2" and the stopwatch on its main page 550.

In one embodiment, the ACT Now App 500 allows a user to initiate termination of a code event using the STOP icon 610. In one embodiment, the user must hold the STOP icon for 3 seconds or longer (to, for example, prevent inadvertent activation of the "STOP" button). In an embodiment, when the user properly initiates termination, the ACT Now App 500 may display additional end options 611 (such as patient death or patient return to normal state). Upon proper input of end options, the ACT Now App 500 records the input with timestamp 612, stops the ACT Now App 500 timer and all active stopwatches, and displays the exit page 614.

In an embodiment, the exit page 614 may allow users to enter additional information. For example, user may provide additional information regarding tubes and IV access points. Such information may be time stamped and delivered to external servers 94. Additional information may also include identification of one or more medical staff. In an embodiment, a physician-specific five letter acronym may be entered to retrieve the user's electronic signature. One or more physician acronyms might be entered. This allows for ICU physicians, residents, or interns to be recorded.

In one embodiment, the ACT Now App 500 may be configured to provide medication suggestions based on user input of patient data or values 592. In one embodiment, the medication suggestions are displayed on the ACT Now App 500 but not displayed on the event device 1.

In one embodiment, the ACT Now App 500 may allow users to request recorded information. For example, the user may have forgotten whether a specific medication or treatment was given (for example, epinephrine), or when or how many times said medication or treatment was given. Upon selecting the RECALL icon 620, the user may be able to select categories of medical events on a display recall options page 621 (for example, selecting "medication" under listed medication and treatment category), and further select specific medical events on a display recall option values page 622 (for example, selecting "epinephrine" under listed medications). Upon proper selection of the information the user wishes to recall, the ACT Now App 500 may provide audio feedback and/or visual display of the information (for example, an audio read-out and/or a video or image display of whether epinephrine was given, and if so, when and how many times).

In one embodiment, the ACT Now App 500 may be updated through downloading new or updated information.

Figure 4E:
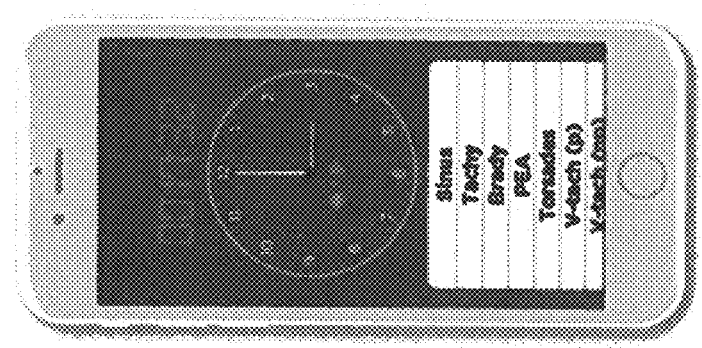
FIGS. 4A-E illustrate embodiments of graphical user interfaces or displays of the software application associated with the event device.
Figure 4D:
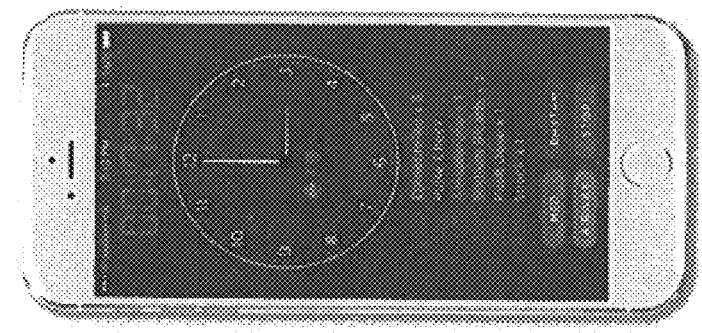
Figure 4C:
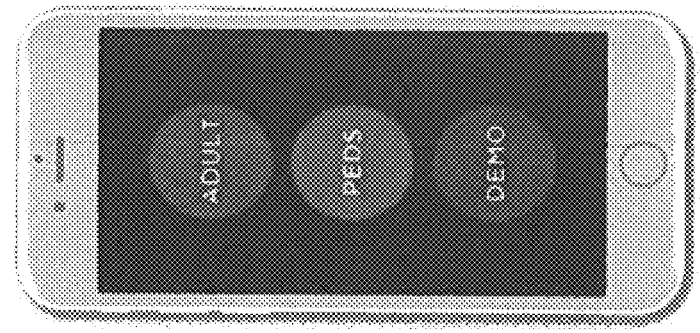
Figure 4B:
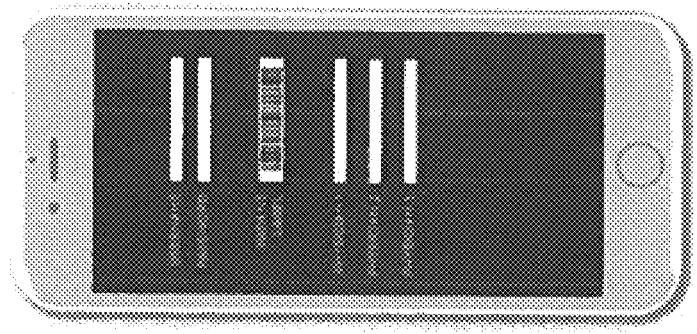
Figure 4A:
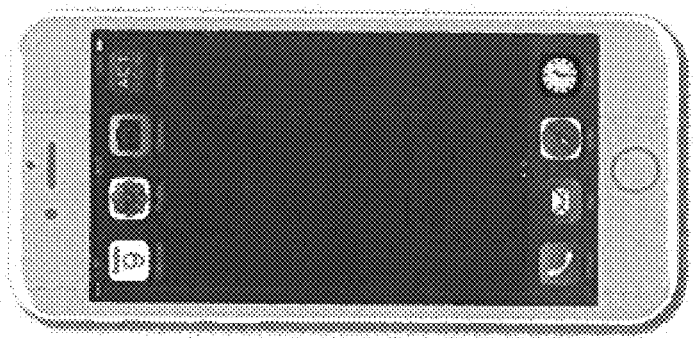

FIG. 4A illustrates the design of an embodiment of the ACT Now icon 510.

FIG. 4B illustrates the design of an embodiment of the user info page 521 where the user can manually enter user credentials 523, and/or the exit page 614 where the user can enter further information and identify additional medical staff present.

FIG. 4C illustrates the design of an embodiment of the patient category selection page 530.

FIG. 4D illustrates the design of an embodiment of the main page 550, which displays analog clock synched up with an event device 1 or event clock 100, any stopwatch and medication information 604, and the MED 600, RHYTHM 580, AIRWAY 570, and STOP 610 icons.

FIG. 4E illustrates the design of an embodiment of the rhythm options display page 581.

FIG. 5 illustrates an embodiment of a system where an ACT Now App 500 might communicate directly with an associated event device 1. On other embodiments, the communication may be indirect, such as via other user devices 92 or external servers 94. As one example, the event device 1 may provide information to an external server 94 which implements a website. The website may, in turn, cause the ACT Now App 500 to receive and display said information. Similarly, the ACT Now App 500 may provide information to an external server 94 which implements a website, which in turn may cause the event device 1 to receive and display said information. An advantage to this system is if the event device 1 malfunctions, each ACT Now App 500 can still communicate with other user devices 81 or external servers 94 to provide information.

Figure 6:
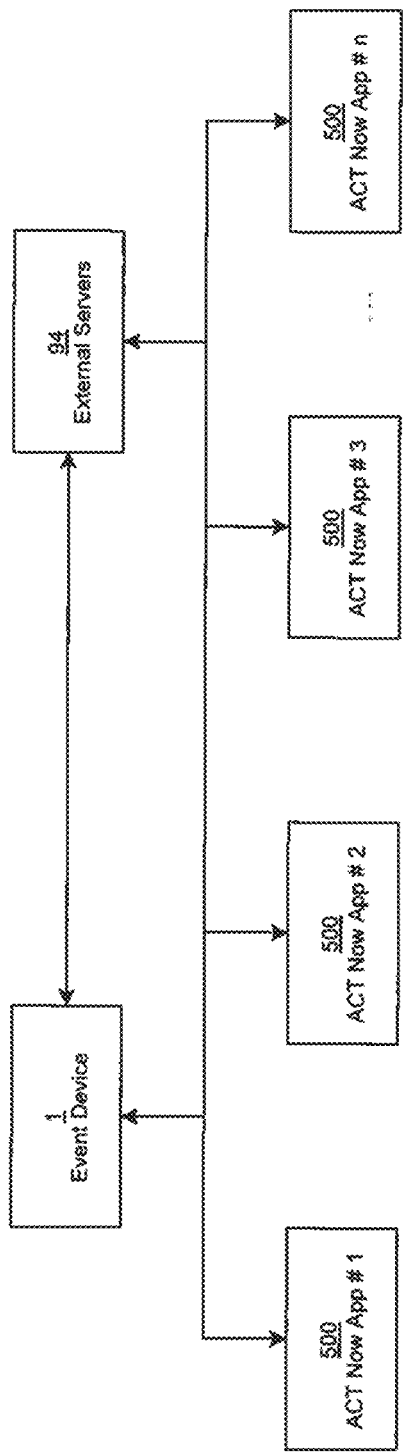
FIG. 6 illustrates the event device in direct and indirect communication with a plurality of software applications.

FIG. 6 illustrates an embodiment of a system where multiple ACT Now Apps 500 are used, each ACT Now App 500 and the event device 1 may be synced such that the event device 1 and all synced ACT Now Apps 500 may be continually updated based upon information received by any input devices 70. For example, an input to the event device 1 may be transmitted to each synced ACT Now App 500. Similarly, an input to an ACT Now App 500 may be transmitted to the event device 1 and each other synced ACT Now Apps 500.

Figure 7:
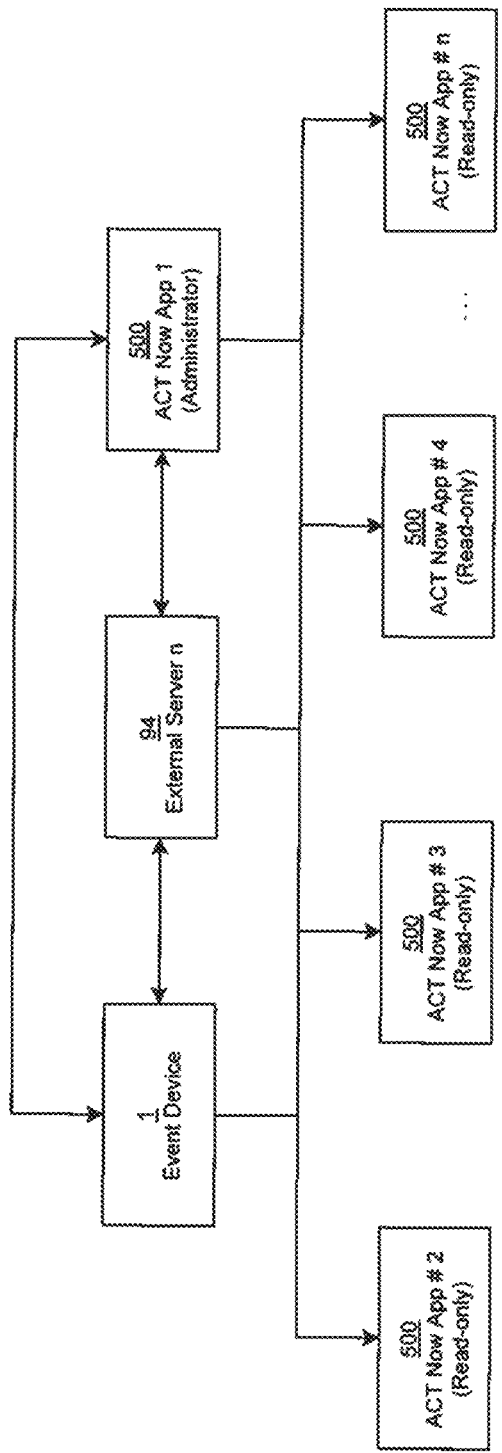
FIG. 7 illustrates the event device in direct and indirect communication with a plurality of software applications, where software applications are set to either administrator mode or read-only mode.

FIG. 7 illustrates an embodiment of a system where one ACT Now App 500 may be designated as the system administrator. In this configuration, only the event device 1 or the administrator ACT Now App 500 may accept user input, while all other ACT Now Apps 500 are set to "view only" mode or status such that the other ACT Now Apps 500 may function as output devices 80 to display recorded information and notifications on their main pages 550, but may not function as input devices 70. This preferred embodiment of the system prevents multiple users from entering duplicative or contradictory input of information.

In a preferred embodiment, users of the ACT Now Apps 500 may be assigned different clearance levels. Depending on the user credential entered 523, 524, the ACT Now Apps 500 may assign a clearance level to the user automatically or by communicate with an external server 84 to retrieve such assignment. Different clearance levels provide or limit the user's access to the type, nature, and/or format of information the user may input, or the ACT Now Apps 500 may display. For example, one clearance level may automatically assign the user of the ACT Now Apps 500 the administrator role mentioned above.

Table 1 in Appendix A illustrates an example of specific use of the event device 1 and ACT Now App 500 during the event code cardiac arrest, including possible time 1000 and corresponding events 1500, possible voice commands 2000 provided to input devices 70 of an event device 1 such as an event clock 100, and corresponding responses, displays, and notifications of medications and treatments due 2500 on the event clock 100. Table 1 also illustrates corresponding user input 3000 to the ACT Now App 500 (due to either user preference or the event device 1 malfunction), and possible responses, displays, and notifications of medications and treatments due 3500 on the ACT Now App 500.

Table 2 in Appendix A illustrates an example of specific use of the event device 1 and ACT Now App 500 during the event code respiratory arrest, including possible events 5000, possible voice commands 5500 provided to input devices 70 of an event device 1 such as an event clock 100, and corresponding responses, displays, and notifications of medications and treatments due 6000 on the event clock 100. Table 2 also illustrates corresponding user input 6500 to the ACT Now App 500 (due to either user preference or the event device 1 malfunction), and possible responses, displays, and notifications of medications and treatments due 7000 on the ACT Now App 500.

As illustrated in the figures and tables referenced above, the devices and system of the invention replace hand-written code sheets and provide a real time, accurate description of resources utilized, medications given, and interventions performed. This information may establish, for example, that every option was exhausted in the event of a death event for legal or malpractice inquiries, or a timestamp of when ROSC was achieved for patient documentation, research, or education. The invention will greatly reduce human error and omissions from hand-written code forms, particularly in hectic and fast-paced code events.

It will be understood that the above-described arrangements of apparatus and the method there from are merely illustrative of applications of the principles of this invention and many other embodiments and modifications may be made without departing from the spirit and scope of the invention as defined in the claims.

TABLE 1

APPENDIX A

| 1000 Time | 1500 Event | 2000 Input to Wall Clock 100 (voice commands) | 2500 Event Clock 100 Response | 3000 Input to ACT Now App 500 | 3500 ACT Now App Response |
|---|---|---|---|---|---|
| Minute 0 | Cardiac arrest patient enters room | "ACT Now on" | Timer begins. | Touch ACT Now icon 510 | Display User Login page 520 |
| | | | | Enter user credentials 521 and 523 or 524, and sync 522 with Wall Clock 100 (if available) | Display Patient Category page 530. |
| | | | | Select Patient Option 531, 532, 533 | Display Time Sync page 540. |
| | | | | Manually enter time 541, 543 or select sync with proximity devices 542, 544, 545 | Begin timer 546. Display Main Page 550. |
| | Apply compression on patient | "Mark compression" | Log compression with timestamp. | Touch CPR icon 560 | Log compression with timestamp 561. |
| | Append bag valve mask on patient | "Mark bag valve mask" | Log airway option (bag valve mask) with timestamp. | Touch AIRWAY icon 570 | Display Airway Options page 571. |
| | | | | Select airway option (bag valve mask) | Log airway option (bag valve mask) with timestamp 573. Return to Main Page 550. |
| Minute 2 | Check patient pulse | "Mark pulse check" | Log pulse check with timestamp. | Touch RHYTHM icon 580 | Display Rhythm Options page 581. |
| | No patient pulse detected. Electrocardiogram displays v-tach rhythm | "Mark rhythm pulseless v-tach" | Log rhythm option (pulseless v-tach) with timestamp. | Select rhythm option (pulseless v-tach) | Log pulse check, rhythm option (pulseless v-tach), and timestamp 582. Return to Main Page 550. |
| | Apply compression on patient | "Mark compression" | Log compression with timestamp | Touch CPR icon 560 | Log compression with timestamp 561 |
| | Intubate patient with 7.5 endotracheal tube, 22 cm at lip | "Mark intubation 7.5 et, 22 cm at lip" | Log airway option (intubation), value (7.5 endotracheal tube, 22 cm at lip), and timestamp. | Touch AIRWAY icon 570 | Display Airway Options page 571. |
| | | | | Select airway option (intubation) | Display intubation values 572. |
| | | | | Select intubation value (7.5 endotracheal tube, 22 cm at lip) | Log airway option (intubation), value (7.5 endotracheal tube, 22 cm at lip), and timestamp 573. Return to Main Page 550. |
| Minute 3 | Physician verbally orders epinephrine. Inject epinephrine | "Mark epi in" | Log medication option (epinephrine) with timestamp. Display solid EPI light. | Touch MED icon 600 | Display Medication Options page 601. |
| | | | | Select medication option (epinephrine) | Log medication option (epinephrine) with timestamp 603. Initiate EPI stopwatch at 0:00 and display "EPI" with stopwatch 604. Return to Main Page 550. |

TABLE 1-continued

APPENDIX A

| 1000 Time | 1500 Event | 2000 Input to Wall Clock 100 (voice commands) | 2500 Event Clock 100 Response | 3000 Input to ACT Now App 500 | 3500 ACT Now App Response |
|---|---|---|---|---|---|
| Minute 4 | Check patient pulse | "Mark pulse check" | Log pulse check with timestamp. | Touch RHYTHM icon 580 | Display Rhythm Options page 581. |
| | No patient pulse detected. Electrocardiogram displays pulseless electrical activity | "Mark rhythm pulseless electrical activity" | Log rhythm option (pulseless electrical activity) with timestamp. | Select rhythm option (PEA) | Log pulse check, rhythm option (PEA), and timestamp 582. Return to Main Page 550. |
| | Apply compression on patient | "Mark compression" | Log compression with timestamp. | Touch CPR icon 560 | Log compression with timestamp 561. |
| Minute 5.5 | 30 seconds until next dose of epinephrine | | Display blinking EPI light. Play "due soon" chirp sounds. | | Displayed "EPI" now blinking. Continue to display EPI stopwatch. Play "due soon" chirp sounds. |
| Minute 6 | Next injection of epinephrine due | | Display blinking EPI light. Play "due now" chirp sounds. | | Displayed "EPI" now blinking. Continue to display EPI stopwatch. Play "due now" chirp sounds. |
| | Inject epinephrine | "Mark epi in" | Log medication option (epinephrine) with timestamp. Display solid EPI light. | Touch MED icon 600 Select medication option (epinephrine) | Display Medication Options page 601. Log medication option (epinephrine) with timestamp 603. Restart EPI stopwatch at 0:00 and display "EPI x2" with stopwatch 604. Return to Main Page 550. |
| | Check patient pulse | "Mark pulse check" | Log pulse check with timestamp. | Touch RHYTHM icon 580 | Display Rhythm Options page 581. |
| | No patient pulse detected. Electrocardiogram displays pulseless electrical activity | "Mark rhythm pulseless electrical activity" | Log rhythm option (pulseless electrical activity) with timestamp. | Select rhythm option (PEA) | Log pulse check, rhythm option (pulseless electrical activity), and timestamp 582. Return to Main Page 550. |
| | Measure patient blood sugar. Patient blood sugar at 30. | "Mark blood sugar 30" | Log patient option (blood sugar) and value (30) with timestamp. | Touch PATIENT icon 590 Select patient option (blood sugar) Select blood sugar value (30) | Display Patient Options page 590. Display blood sugar values 592. Log patient option (blood sugar), value (30), and timestamp 593. Return to Main Page 550. |
| | Apply compression on patient | "Mark compression" | Log compression with timestamp | Touch CPR icon 560 | Log compression with timestamp 561. |
| | Automatic suggestion for D50 IV push. | | Display blinking D50 light. Play "due soon" chirp sounds. | | Display blinking "D50 IV Push". Play "due soon" chirp sounds. |
| Minute 7 | Physician verbally orders D50 and Calcium. Apply D50. | "Mark D50 in" | Log medication option (D50) with timestamp. Display solid D50 light. | Touch MED icon 600 Select medication option (D50) | Display Medication Options page 601. Log medication option (D50) with timestamp 603. Initiate D50 stopwatch at 0:00 and display "D50" with stopwatch 604. Return to Main Page 550. |
| | Apply Calcium | "Mark Calcium in" | Log medication option (Calcium) with timestamp. Display solid Calcium light. | Touch MED icon 600 Select medication option (Calcium) | Display Medication Options page 601. Log medication value (Calcium) with timestamp 603. Initiate Calcium stopwatch at 0:00 and display "Calcium" with stopwatch 604. Return to Main Page 550. |
| Minute 8 | Check patient pulse. | "Mark pulse check" | Log pulse check with timestamp. | Touch RHYTHM icon 580 | Display Rhythm Options page 581. |
| | No patient pulse detected. Electrocardiogram displays pulseless v-tach activity. | "Mark rhythm pulseless v-tach" | Log rhythm option (pulseless v-tach) with timestamp. | Select rhythm option (pulseless v-tach) | Log pulse check, rhythm option (pulseless v-tach), and timestamp 582. Return to Main Page 550. |
| | Physician verbally orders shock. Staff exit room. Apply shock. | "Mark shock given" | Log "shock x1" with timestamp. Display "1" under Shock icon. | Touch SHOCK icon 565 | Log "shock x1" with timestamp 566. Display "Shock x1" 567. |
| | Check patient pulse. | "Mark pulse check" | Log pulse check with timestamp. | Touch RHYTHM icon 580 | Display Rhythm Options page 581. |
| | No patient pulse detected. Electrocardiogram displays pulseless v-tach activity. | "Mark rhythm pulseless v-tach" | Log rhythm option (pulseless v-tach) with timestamp. | Select rhythm option (pulseless v-tach) | Log pulse check, rhythm option (pulseless v-tach), and timestamp 582. Return to Main Page 550. |
| | Apply compression on patient | "Mark compression" | Log compression with timestamp. | Touch CPR icon 560 | Log compression with timestamp 561. |

TABLE 1-continued

APPENDIX A

| 1000 Time | 1500 Event | 2000 Input to Wall Clock 100 (voice commands) | 2500 Event Clock 100 Response | 3000 Input to ACT Now App 500 | 3500 ACT Now App Response |
|---|---|---|---|---|---|
| Minute 8.5 | 30 seconds until next dose of epinephrine | | Display blinking EPI light. Play "due soon" chirp sounds. | | Displayed "EPIx2" now blinking. Continue to display EPI stopwatch. Play "due soon" chirp sounds. |
| | Physician verbally orders 300 mg Amiodarone | "Mark 300 mg Amiodarone bolus" | Log medication option (Amiodarone) and value (300 mg) with timestamp. Display solid Amiodarone light. | Touch MED icon 600 Select medication option (Amiodarone) Select Amiodarone values (300 mg). | Display Medication Options page 601. Display Amiodarone values 602. Log medication option (Amiodarone) and value (300 mg) with timestamp 603. Initiate Amiodarone stopwatch at 0:00 and display "Amiodarone" stopwatch with 604. Return to Main Page 550. |
| Minute 9 | Next injection of epinephrine due | | Display blinking EPI light. Play "due now" chirp sounds. | | Displayed "EPIx2" now blinking. Continue to display EPI stopwatch. Play "due now" chirp sounds. |
| | Inject epinephrine | "Mark epi in" | Log application of medication (epinephrine) with timestamp. Display solid EPI light. | Touch MED icon 600 Select medication option (epinephrine) | Display Medication Options page 601. Log medication option (epinephrine) with timestamp 603. Restart EPI stopwatch at 0:00 and display "EPI x3" with stopwatch 604. Return to Main Page 550. |
| Minute 10 | Check patient pulse. | "Mark pulse check" | Log pulse check with timestamp. | Touch RHYTHM icon 580 | Display Rhythm Options page 581. |
| | No patient pulse detected. Electrocardiogram displays torsades. | "Mark rhythm torsades" | Log rhythm option (torsades) with timestamp. | Select rhythm option (torsades) | Log pulse check, rhythm option (torsades), and timestamp 582. Return to Main Page 550. |
| | Physician verbally orders shock. Staff exit room. Apply shock. | "Mark shock given" | Log "shock x2" with timestamp. Display "2" under Shock icon. | Touch SHOCK icon 565 | Log "shock x2" with timestamp 566. Display "Shock x2" 567. |
| | Physician verbally orders 1 g Magnesium | "Mark 1 g magnesium in" | Log medication option (Magnesium) and value (1 g) with timestamp. Display solid Magnesium light. | Touch MED icon 600 Select medication (Magnesium) Select Magnesium value (1 g) | Display Medication Options page 601. Display Magnesium values 602. Log medication option (Magnesium) and value (1 g) with timestamp 603. Initiate Magnesium stopwatch at 0:00 and display "Magnesium" with stopwatch 604. Return to Main Page 550. |
| Minute 11.5 | 30 seconds until next dose of epinephrine | | Display blinking EPI light. Play "due soon" chirp sounds. | | Displayed "EPIx3" now blinking. Continue to display EPI stopwatch. Play "due soon" chirp sounds. |
| Minute 12 | Next injection of epinephrine due | | Display blinking EPI light. Play "due now" chirp sounds. | | Displayed "EPIx3" now blinking. Continue to display EPI stopwatch. Play "due now" chirp sounds. |
| | Epinephrine not given | | Display blinking EPI light. | | Displayed "EPIx3" now blinking. Continue to display EPI stopwatch. |
| | Check patient pulse. | "Mark pulse check" | Log pulse check with timestamp | Touch RHYTHM icon 580 | Display Rhythm Options page 581. |
| | Patient pulse detected. Electrocardiogram displays sinus tachycardia. | "Mark rhythm sinus-tach" | Log rhythm option (sinus tachycardia) with timestamp. | Select rhythm option (sinus tachycardia) | Log pulse check, rhythm option (sinus tachycardia), and timestamp 582. Return to Main Page 550. |
| Minute 14 | Pulse lost. Electrocardiogram displays pulseless electrical activity. | "Mark rhythm pulseless electrical activity" | Log rhythm option (pulseless electrical activity) with timestamp. | Touch RHYTHM icon 580 Select PEA option | Display Rhythm Options page 581. Log pulse check, rhythm option (pulseless electrical activity), and timestamp 582. Return to Main Page 550. |
| | Apply compression on patient | "Mark compression" | Log compression with timestamp. | Touch CPR icon 560 | Log compression with timestamp 561. |
| | Inject epinephrine | "Mark epi in" | Log medication option (Epinephrine) with timestamp. Display solid EPI light. | Touch MED icon 600 Select medication (epinephrine) | Display Medication Options page 601. Log application of medication (epinephrine) with timestamp. |

TABLE 1-continued

APPENDIX A

| 1000 Time | 1500 Event | 2000 Input to Wall Clock 100 (voice commands) | 2500 Event Clock 100 Response | 3000 Input to ACT Now App 500 | 3500 ACT Now App Response |
|---|---|---|---|---|---|
| | | | | | Restart EPI stopwatch at 0:00 and display "EPI x4" with stopwatch 604. Return to Main Page 550. |
| | Continue cycling until physical orders termination of code or return of spontaneous circulation is achieved | | | | |
| | End code due to patient death | "Mark end code TOD" | Log stop value (patient death) with timestamp. Stop timer. | Hold STOP icon 610 for 3 seconds Select end option (TOD) | Display End Options page 611. Log end option (patient death) with timestamp 612. Stop timer 613. Display Exit Page 614. |
| | | "Mark end code ROSC" | | Hold STOP icon 610 for 3 seconds | Display End Options page 611. |
| | Alternatively, end code upon return of spontaneous circulation | | Log stop value (return of spontaneous circulation) with timestamp. Stop timer. | Select end option (ROSC) | Log end option (return of spontaneous circulation) with timestamp 612. Stop timer 613. Display Exit Page 614. |

TABLE 2

| 5000 Event | 5500 Input to Wall Clock 100 (voice commands) | 6000 Event Clock 100 Response | 6500 Input to ACT Now App 500 | 7000 ACT Now App Response |
|---|---|---|---|---|
| Respiratory arrest patient enters room. Patient respirations <8/min. | "ACT Now on" | Timer begins. | Touch ACT Now icon 510 Enter user credentials 521, 523, 524 and sync 522 with Wall Clock 100 (if available) Select Patient Option 531, 532, 533 Manually enter time 541, 543 or select sync with proximity devices 542, 544, 545 | Display User Login page 520 Display Patient Category page 530. Display Time Sync page 540. Begin timer 546. Display Main Page 550. |
| Physician verbally orders Rapid Sequence Intubation medications | "Mark Etomidate in" | Log medication option (Etomidate) with timestamp Display solid Etomidate light. | Touch MED icon 600 Select medication option (Etomidate) | Display Medication Options page 601. Log medication option (Etomidate) with timestamp 603. Initiate Etomidate stopwatch at 0:00 and display Etomidate stopwatch 604. Return to Main Page 550. |
| | "Mark continuous drip sedation in" | Log medication option (Continuous Drip Sedation) with timestamp. Display solid Etomidate light. | Touch MED icon 600 Select medication option (Continuous Drip Sedation) | Display Medication Options page 601. Log medication option (Continuous Drip Sedation) with timestamp 603. Initiate Continuous Drip Sedation stopwatch at 0:00 and display Continuous Drip Sedation stopwatch 604. Return to Main Page 550. |
| Sedate patient | "Mark patient sedated" | Log patient option (Sedated) with timestamp. | Touch PATIENT icon 590. Select patient option (Sedated) | Display Patient Options page 591. Log patient option (Sedated) with timestamp 593. Return to Main Page 550. |
| Intubate patient with 7.5 endotracheal tube, 24 cm at lip | "Mark 7.5 et, 24 cm at lip" | Log airway option (intubation) and value (7.5 endotracheal tube, 24 cm at the lip) with timestamp. | Touch AIRWAY icon 570. Select airway option (Intubation) Select intubation values | Display Airway Options page 571. Display intubation values 572. Log airway option (intubation), value (7.5 endotracheal tube, 22 cm at lip), and timestamp 573. Return to Main Page 550. |
| Patient ventilated well | "Mark vent settings AC mode, vt 450, O2 | Log airway option (ventilator) and value (AC mode, vt 450, O2 100%, Peep 5, R 8) with | Touch AIRWAY icon 570. Select airway option (ventilator) | Display Airway Options page 571. Display ventilator values 572. |

TABLE 2-continued

| 5000 Event | 5500 Input to Wall Clock 100 (voice commands) | 6000 Event Clock 100 Response | 6500 Input to ACT Now App 500 | 7000 ACT Now App Response |
|---|---|---|---|---|
| | 100%, PEEP 5, R 18" | timestamp. | Select enter ventilator value (AC mode, vt 450, O2 100%, Peep 5, R 8) | Log airway option (ventilator), value (AC mode, vt 450, O2 100%, Peep 5, R 8), and timestamp 573. Return to Main Page 550. |
| Check patient pulse | "Mark pulse check" | Log pulse check with timestamp. | Touch RHYTHM icon 580. | Display Rhythm Options page 581. |
| Electrocardiogram displays normal sinus | "Mark rhythm sinus" | Log rhythm value (normal sinus) with timestamp. | Select rhythm option (normal sinus). | Log pulse check, rhythm value (normal sinus), and timestamp 582. Return to Main Page 550. |
| End code | "Mark end code" | Stop timer. | Hold STOP icon 610 for 3 seconds | Display End Options page 611. |
| | | | Select end option (patient normal) | Log end option (patient normal) with timestamp 612. Stop timer 613. Display Exit Page 614. |

The invention claimed is:

1. A medical code event tracking and generating system comprising:
 a server comprising a processor, a memory and machine-readable code stored in said memory and executable by said processor thereof;
 a downloadable code event application comprising machine readable code configured to be transmitted to and installed in a memory of each of a plurality of user devices operated by code event medical personnel, said user devices comprising a mobile communication device comprising a housing, a processor, said memory, a user input device, and a display, wherein said downloaded code event application is executable by said processor thereof;
 said machine-readable code stored in said memory of said server configured to cause said processor of said server thereof to:
  receive, from at least one of said plurality of user devices, information identifying at least one medical personnel associated with the medical code event;
  receive, from at least one of said plurality of user devices, information identifying said patient;
  receive, from at least one of said plurality of user devices, information regarding a code event action;
  receive measured patient value information from at least one medical monitoring device associated with said patient;
  create, for said medical code event, a code event record for said patient in response to receiving said information regarding said code event action;
  process said information regarding said code event action, said measured patient value information and/or input or stored patient data, to generate medical treatment information regarding a suggested medical treatment to be administered to said patient at a future time based upon said code event action;
  cause said plurality of user devices to display, via the code event applications running therein, on the displays thereof, a clock face displaying time indicia and one or more time indicators movable relative to said time indicia, one or more electronic display elements comprising at least one patient value indicator configured to display at least one measured patient value, one or more medical treatment indicators, and a plurality of medication indicators configured to display information regarding one or more administered medications and generated medications, wherein said time indicia comprise individual minute indicating indicia and said medication indicators are associated with said minute indicating indicia to display a graphical indication of a timing thereof;
  cause, via the code event applications running on said plurality of user devices, on the displays thereof, said generated medical treatment information to be displayed via at least one of said one or more medical treatment indicators and medication indicators, and a timing thereof;
  receive input regarding the administration of at least one of said medical treatments or medications displayed by said plurality of user devices via input to at least one of said plurality of user devices;
  utilize said information regarding said code event action, said measured patient value information and/or said input or stored information regarding said patient, and said information regarding said administered medical treatment or medication, to generate updated medical treatment information;
  automatically generate an output of said updated medical treatment information which causes, via said code event applications running on said user devices, said user devices to display said updated medical treatment information via said one or more medical treatment indicators and medication indicators and a timing thereof; and
  store, in association with said code event record, said information identifying said one or more medical personnel, an electronic signature of a physician, said information identifying said patient, said measured patient value information, said information regarding said code event action, information regarding said administered medical treatment, said generated medical treatment information and said updated medical treatment information, wherein said measured patient value information, said information regarding said code event action, and information regarding said administered medical treatment are time-stamped.

2. The system in accordance with claim 1, wherein said plurality of medication indicators comprise a plurality of color-coded indicators which identify different medications at each of said individual minute indicating indicia.

3. The system in accordance with claim 1, wherein said displaying comprises illuminating a color-coded indicator which identifies a particular medication at a particular time corresponding to at least one of said minute indicating indicia displayed by said user device.

4. The system in accordance with claim 1, wherein said measured patient value information comprises at least one of heart rate, cardiac rhythm and blood pressure.

5. The system in accordance with claim 1, wherein said information regarding said code event action comprises information designating a code blue event.

6. The system in accordance with claim 1, wherein said generated medical treatment information comprises at least one of CPR, electrical shocks, a pulse check, and a medication.

7. The system in accordance with claim 1, further comprising a code event device which is communicatively linked to said server, said code event device comprising a housing, a clock associated with said housing, said clock comprising a face displaying time indicia and one or more time indicators movable relative to said time indicia, one or more electronic display elements comprising at least one patient value indicator configured to display at least one measured patient value, one or more medical treatment indicators, and a plurality of medication indicators configured to display information regarding one or more administered medications and generated medications, wherein said time indicia comprise individual minute indicating indicia and said medication indicators are associated with said minute indicating indicia to display a graphical indication of a timing thereof, a processor, an audio input device, an audio output device, a memory, a communication interface, and machine-readable code stored in said memory and executable by said processor.

8. The system in accordance with claim 7, wherein said generated medical treatment information is also displayed via at least one of said one or more medical treatment indicators and medication indicators of said code event device.

9. The system in accordance with claim 7, wherein said code event device is configured as a wall clock which is configured to be supported on wall and has physical time indicators.

10. The system in accordance with claim 1, wherein said information regarding said code event action comprises input to a code event icon displayed by said display of said user device by said code event application.

11. The system in accordance with claim 1, wherein said information regarding said medical code event is time-stamped by said user device.

12. The system in accordance with claim 1, wherein said clock face is displayed on said displays of said user devices as part of a graphical user interface.

13. A method for medical code event tracking, comprising the steps of:
  downloading a downloadable code event application comprising machine readable code configured to be transmitted to and installed in a memory of each of a plurality of user devices operated by code event medical personnel;
  configuring machine-readable code stored in a memory of a server to cause a processor of the server thereof to:
    receiving, at the server comprising said processor, said memory and said machine-readable code stored in said memory and executable by said processor thereof, from at least one of said plurality of user devices comprising a mobile communication device comprising a housing, a processor, said memory, a user input device, and a display, and a downloaded code event application stored in the memory and executable by said processor thereof, information identifying at least one medical personnel associated with the medical code event;
    receiving, from at least one of said plurality of user devices, at said server, information identifying said patient;
    receiving, from at least one of said plurality of user devices, at said server, information regarding a code event action;
    receiving, at said server, measured patient value information from at least one medical monitoring device associated with said patient;
    creating, at said server, for said medical code event, a code event record for said patient in response to receiving said information regarding said code event action;
    processing, at said server, said information regarding said code event action, said measured patient value information and/or input or stored patient data, to generate medical treatment information regarding a suggested medical treatment to be administered to said patient at a future time based upon said code event action;
    causing, via interaction between said server and said code event applications running on said plurality of user devices, said plurality of user devices to display, via the code event applications running therein, on the displays thereof, a clock face displaying time indicia and one or more time indicators movable relative to said time indicia, one or more electronic display elements comprising at least one patient value indicator configured to display at least one measured patient value, one or more medical treatment indicators, and a plurality of medication indicators configured to display information regarding one or more administered medications and generated medications, wherein said time indicia comprise individual minute indicating indicia and said medication indicators are associated with said minute indicating indicia to display a graphical indication of a timing thereof;
    causing, via the code event applications running on said plurality of user devices, on the displays thereof, said generated medical treatment information to be displayed via at least one of said one or more medical treatment indicators and medication indicators, and a timing thereof;
    receiving, at said server, input regarding the administration of at least one of said medical treatments or medications displayed by said plurality of user devices via input to at least one of said plurality of user devices;
    utilizing, at said server, said information regarding said code event action, said measured patient value information and/or said input or stored information regarding said patient, and said information regarding said administered medical treatment or medication, to generate updated medical treatment information;
    automatically generating, via said server, an output of said updated medical treatment information which causes, via said code event applications running on said user devices, said user devices to display said updated medical treatment information via said one or more medical treatment indicators and medication indicators and a timing thereof; and storing, in association with said code event record, said information identifying said one or more medical personnel, an electronic signature of a physician, said information identifying said patient, said measured patient value information, said information regarding said code event action, information regarding said administered medical treatment, said generated medical treatment information and said updated medical treatment information, wherein said measured patient value information, said information regarding said code event action, and information regarding said administered medical treatment are time-stamped.

14. The method in accordance with claim 13, wherein said plurality of medication indicators comprise a plurality of color-coded indicators which identify different medications at each of said individual minute indicating indicia.

15. The method in accordance with claim 13, wherein said displaying comprises illuminating a color-coded indicator which identifies a particular medication at a particular time corresponding to at least one of said minute indicating indicia displayed by said user device.

16. The method in accordance with claim 13, wherein said measured patient value information comprises at least one of heart rate, cardiac rhythm and blood pressure.

17. The method in accordance with claim 13, wherein said information regarding said code event action comprises information designating a code blue event.

18. The method in accordance with claim 13, wherein said generated medical treatment information comprises at least one of CPR, electrical shocks, a pulse check, and a medication.

19. The method in accordance with claim 13, further comprising the step of causing said at generated medical treatment information to be displayed via at least one medical treatment indicator and medication indicator of a code event device which is communicatively linked to said server, said code event device comprising a housing, a clock associated with said housing, said clock comprising a face displaying time indicia and one or more time indicators movable relative to said time indicia, one or more electronic display elements comprising at least one patient value indicator configured to display at least one measured patient value, said one or more medical treatment indicators, and said medication indicators configured to display information regarding one or more administered medications and generated medications, wherein said time indicia comprise individual minute indicating indicia and said medication indicators are associated with said minute indicating indicia to display a graphical indication of a timing thereof, a processor, an audio input device, an audio output device, a memory, a communication interface, and machine-readable code stored in said memory and executable by said processor.

20. The method in accordance with claim 13, wherein said information regarding said code event action comprises input to a code event icon displayed by said display of said user device by said code event application.

\* \* \* \* \*